United States Patent [19]
Hannon et al.

[11] Patent Number: 5,116,335
[45] Date of Patent: May 26, 1992

[54] INTRAMEDULLARY HYBRID NAIL AND INSTRUMENTATION FOR INSTALLATION AND REMOVAL

[76] Inventors: Gerard T. Hannon, 6 Standish Dr., Scarsdale, N.Y. 10583; James Molnar, deceased, late of Trumbull; Lucienne Molnar, executrix, 25 Clemons Ave., Trumbull, both of Conn. 06611

[21] Appl. No.: 408,874

[22] Filed: Sep. 18, 1989
(Under 37 CFR 1.47)

[51] Int. Cl.$^5$ .............................................. A61F 5/04
[52] U.S. Cl. .......................................... 606/62; 606/63
[58] Field of Search .................... 606/60, 61, 62, 63, 606/64, 65, 66, 67, 68

[56] References Cited

U.S. PATENT DOCUMENTS

| | | | |
|---|---|---|---|
| 3,977,398 | 8/1976 | Burstein | 606/62 |
| 4,237,875 | 12/1980 | Termanini | 606/63 |
| 4,522,200 | 6/1985 | Stednitz | 606/63 |
| 4,728,333 | 3/1988 | Masse | 606/63 |
| 4,858,602 | 8/1989 | Seidel | 606/60 |
| 4,919,678 | 4/1990 | Kranz | 606/63 |

*Primary Examiner*—Robert A. Hafer
*Assistant Examiner*—Michael Brown
*Attorney, Agent, or Firm*—Pasquale A. Razzano

[57] ABSTRACT

An intramedullary device for use in internal fixation of a fracture transverse to the longitudinal axis of a long bone which includes a substantially rigid center rod having a plurality of longitudinal slots extending along the length thereof. One of a plurality of generally flexible outer rods is received and retained within one of the longitudinal slots and thereby extend outwardly from the center rod. Each outer rod has a retention section angulated from the longitudinal axis of the long bone which penetrates through and is retained by the cancellous bone thereby stabilizing the fracture at the distal and proximal ends of the long bone. In order to install the intramedullary device within the endosteal canal, each end of the generally flexible outer rods are coupled to one of a plurality of extension rods of an installation device. The generally rigid center rod is introduced through the central opening of the installation device and thus extends into the endosteal canal. As the center rod is moved into the endosteal canal, each of the outer rods is slidably engaged into one of the plurality of longitudinal slots of the center rod. This movement forces the cutting edge of each outer rod to penetrate through the cancellous bone and allows the retention section of the outer rods to be retained within the cancellous bone thereby stabilizing the fracture of the long bone.

25 Claims, 4 Drawing Sheets

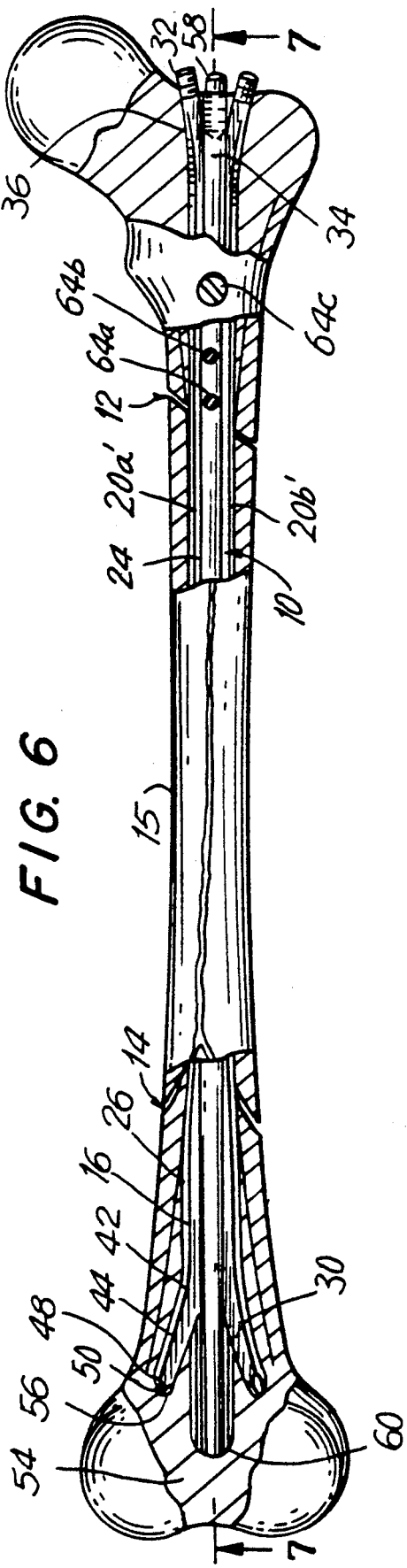
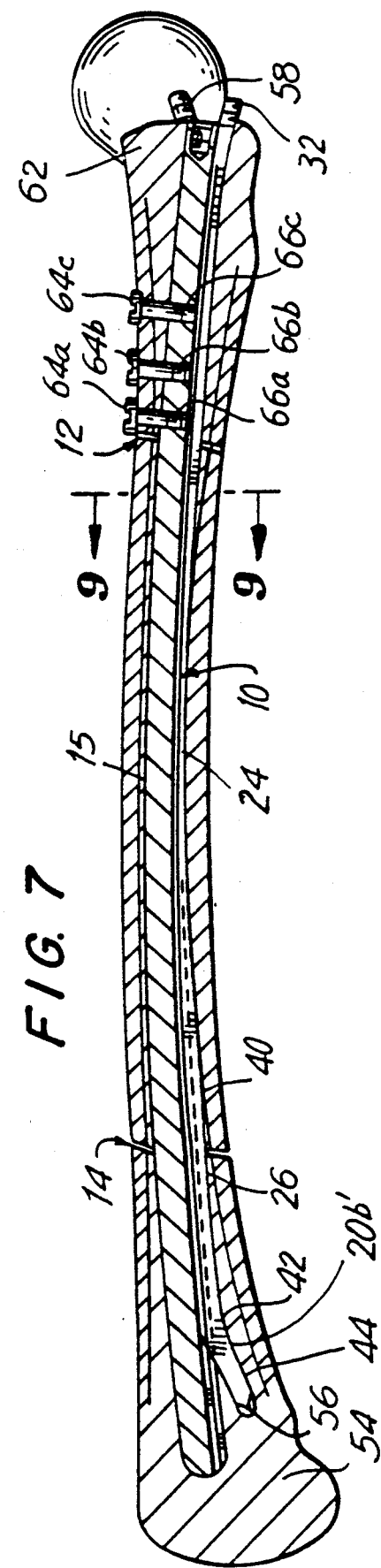
FIG. 6
FIG. 7

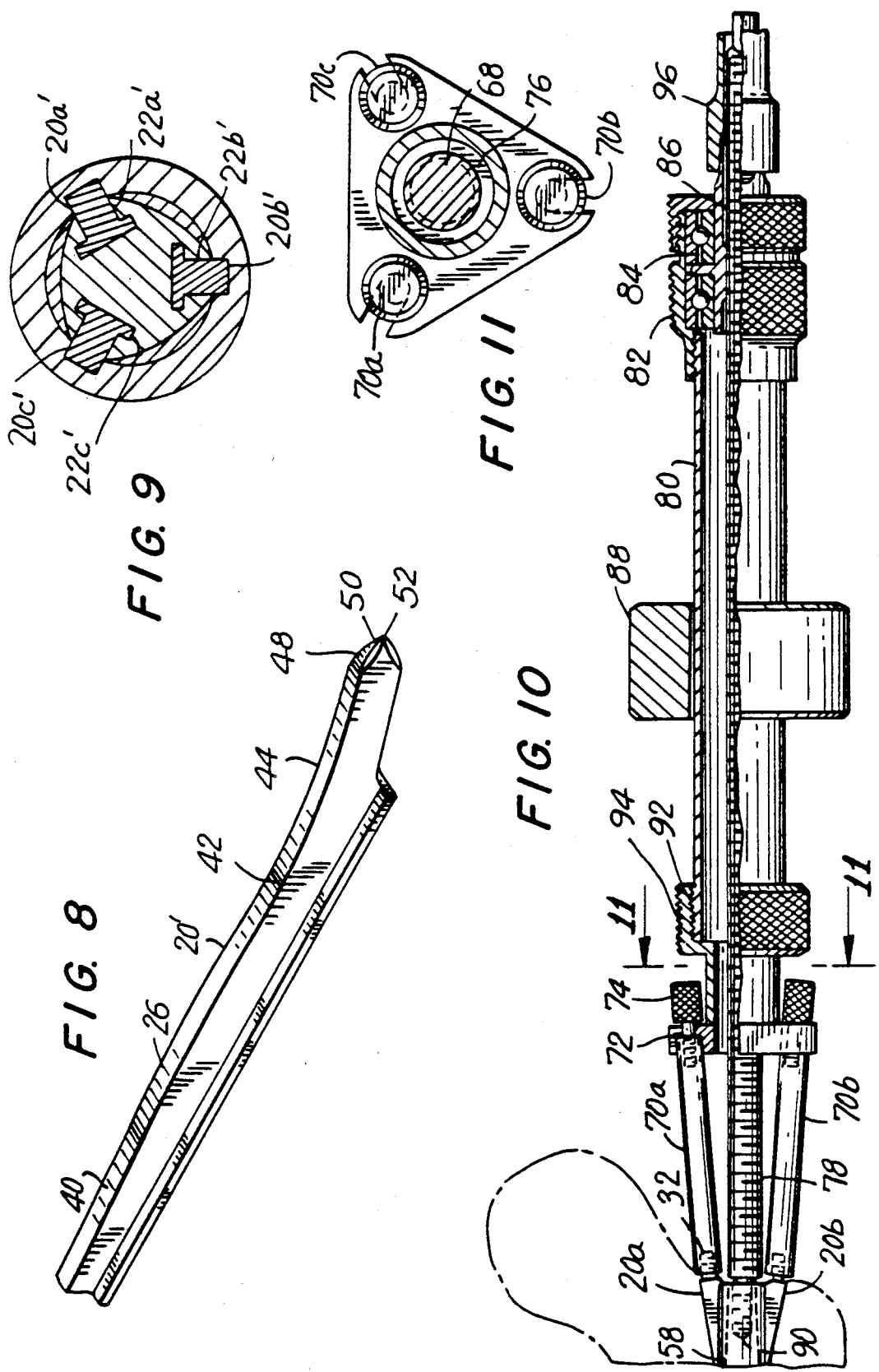

INTRAMEDULLARY HYBRID NAIL AND INSTRUMENTATION FOR INSTALLATION AND REMOVAL

FIELD OF THE INVENTION

This invention relates to the internal fixation of long bones (i.e. femur, tibia, humerus, etc.) particularly the proximal and distal regions, using a combination (hybrid) of a fairly rigid center rod in conjunction with a number of fairly flexible outer rods.

BACKGROUND OF THE INVENTION

Intramedullary (IM) nailing or fixation has enjoyed a tremendous amount of clinical success over the last 40 years. Modern IM nailing as it is known today began during World War II with the work of Gerhard Kuntscher in Germany. Kuntscher's nail and method worked for primarily two reasons. First, the hardware provided stable fixation allowing early mobilization of the patient while the fracture had time to heal. Secondly, the method was that of closed nailing with the incision and point of entry into the femoral canal far removed from the actual fracture site.

This closed method limits the damage to soft tissues and blood supply overlying the fracture and hence greatly reduces the risk of infection and/or possible nonunion. Kuntscher's original method is however limited in that it does not rigidly hold a fracture in the proximal or distal regions of the femoral shaft. The reason for this is that Kuntscher's nail has a constant cross section. Unfortunately the endosteal canal of the femur (for that matter of all long bones) is a constant cross section over a limited length-typically the middle one-third of the shaft. The endosteal canal enlarges or expands in the proximal one-third of the shaft and particularly the distal one-third regions of all long bones.

In an attempt to solve this problem in the case of the femur a number of IM devices have evolved over the years. The current state of the art with regards to IM fixation of these proximal and distal femur fractures is such that it is handled by a number of different methods. Some inventors have designed a specific device to internally fix a specific fracture pattern. Zickel designed a subtrochanteric nail (U.S. Pat. No. 3,433,220) for the fixation of subtrochanteric fractures as well as a supracondylar nail (U.S. Pat. No. 4,011,863) for the fixation of supracondylar fractures. Fischer, et al. (U.S. Pat. Nos. 3,759,257; 3,760,802; 3,799,239) all are primarily directed at fixation of fractures in the metaphyseal region of long bones. Aginsky (U.S. Pat. Nos. 4,091,806 and 4,227,518) discloses at least in part some of the problems associated with proximal and distal fixation without employing any interlocking principle. The interlocking principle has been applied to these fracture patterns over the last decade. It involves the use of an IM rod which contains holes proximally and distally through which transfixion screws are inserted in order to obtain stability of proximal and/or distal fracture patterns as well as fractures involving the middle one-third of the shaft. Examples here being the Klemm-Schellmann, Grosse-Kempf, Russel-Taylor, Williams (U.S. Pat. No. 4,697,585) and the Brooker-Wills (U.S. Pat. No. 4,519,100) systems. Finally, multiple Ender pins (U.S. Pat. No. 4,169,470) which are a classic example of flexible pinning is being used more frequently for fixation of shaft and distal femoral fractures using a method known as "bundle nailing".

While many of the above-mentioned devices have been beneficial in the treatment of various fracture patterns, they have some distinct disadvantages. Some of the "specific devices" mentioned are so specific that they are only beneficial in the treatment of a specific fracture pattern and not to other fractures involving the shaft of a long bone. Others are complicated mechanically having several moving parts which may or may not work in an "in vivo" environment. Still others fail to appreciate lessons learned from authorities like Frederic Rhinelander on the vascular response of bone to internal fixation. The interlocking nails are popular but have some definite disadvantages. For example, the problems of distal screw fixation, as yet unsolved, are that they cannot be easily instrumentated, require significant teaching of the technique which involves additional radiation exposure to the surgical team, and lastly, inherently weaken the IM portion of the device.

OBJECTS OF THE INVENTION

Therefore, it is an object of the present invention to provide an IM fixation system which avoids the above-described difficulties of the prior art.

It is another object of the present invention to provide an IM fixation system which provides excellent stability in three planes of motion for varying fracture patterns of long bones, including superior torsional rigidity throughout the length of the endosteal canal.

It is yet another object of the present invention to provide an IM fixation system which is installed through a single proximal incision in a completely closed fashion.

It is still another object of the present invention to provide an IM fixation system which does not involve the aforementioned interlocking principle.

The present invention is directed towards solving the problems of proximal and distal fracture fixation while also managing fractures of the middle region of long bones. It is simple, the implanted device contains no moving parts, provides a workable solution which should be fairly economical to manufacture.

These and other objects, aspects and features of the present invention will become apparent from the following detailed description thereof taken in conjunction with the accompanying drawings, throughout which like reference numerals denote like elements and parts.

SUMMARY OF THE INVENTION

The intramedullary fixation device of this invention is a hybridization of flexible and rigid nailing incorporating many of the proven advantages of each method while attempting to eliminate the disadvantage of prior systems.

The IM device consists of primarily four rods–one substantially rigid center rod and three generally flexible outer rods arranged at approximately 120 degree intervals around the center rod giving the implanted fixation device a "triflange" appearance. The center rod has a plurality of longitudinal slots extending along the length thereof. Each of the flexible outer rods is received and retained within one of these longitudinal slots. The flexible outer rods have a shape corresponding to that of the slots in the center rod thus insuring a very positive fit between the center rod and each of the flexible rods.

These flexible outer rods along the middle of their length have a straight inner and outer flat edge which are essentially parallel to each other. However, at the proximal and to a much greater degree at the distal ends of each flexible rod the rod angulates away from the inner edge at a predetermined distance similar to the manner in which the endosteal canal of the long bone enlarges or expands in the proximal and distal regions. This first angulated retention section diverges from the longitudinal axis of the long bone at the distal end and penetrates through and is retained by the cancellous bone thereby stabilizing the fracture at the distal and proximal ends of the long bone. This first retention section has a cutting edge generally in the form of a rounded arrowpoint at its free end aiding the retention section in its ability to penetrate into the cancellous bone. A second angulated retention section diverges from the longitudinal axis of the long bone at its proximal end which penetrates through the cancellous bone and cooperates with the first angulated retention section to stabilize the fractures at the distal and proximal ends of the long bone. This structure in conjunction with the design of the center rod and the manner in which the intramedullary device is installed enables the device "to expand" in the proximal and distal regions of a long bone internally fixing it along the length of the endosteal canal.

A new and unique installation device is also provided to be used in conjunction with the intramedullary device of this invention. The installation device has a plurality of extension rods and a central opening. The generally flexible outer rods of the IM device are coupled to the installation device and extend into the endosteal canal with an end of each outer rod being cooperatively engaged by one of the extension rods and the other end having a cutting edge, as described above. The generally rigid center rod is introduced through the central opening of the installation device and thus into the endosteal canal. As the center rod is advanced into the endosteal canal, each of the outer rods is slidably engaged into one of the plurality of longitudinal slots of the center rod. This movement forces the first angulated retention section of each outer rod to penetrate through the cancellous bone and permit the first and second angulated retention sections of the outer rods to be retained within the cancellous bone thereby stabilizing the fracture along the entire length of the long bone.

BRIEF DESCRIPTION OF THE DRAWINGS

The following detailed description, given by way of example but not intended to limit the invention solely to the specific embodiments described, may best be understood in conjunction with the accompanying drawings in which:

FIG. 6 is a front cross-sectional view of a second preferred embodiment of an intramedullary device of the present invention installed within a long bone.

FIG. 7 is a front cross-sectional lateral view taken along line 7—7 of FIG. 6 wherein a flexible outer rod extends outwardly from a central inner rod.

FIG. 8 is a front cutaway perspective view of a preferred embodiment for the distal end of the flexible outer rods of FIGS. 6 and 7.

FIG. 9 is a side cross-sectional view taken along line 9—9 of FIG. 7.

FIG. 10 is a front elevational view of a preferred embodiment of an intramedullary installation device used in conjunction with the intramedullary devices of FIGS. 1-9.

FIG. 11 is a side elevational view taken along line 11—11 of FIG. 10.

DESCRIPTION OF THE PREFERRED EMBODIMENT

Figure 5:
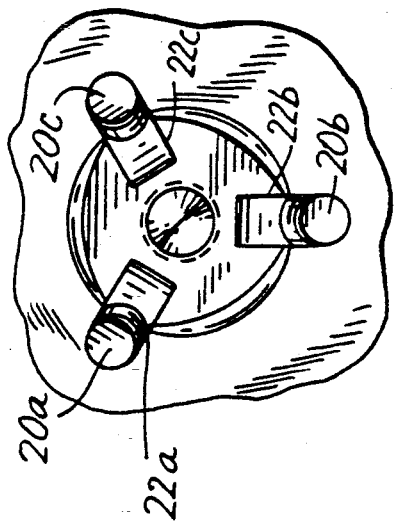
FIG. 5 is a side cross-sectional view taken along line 5—5 of FIG. 3.
Figure 4:
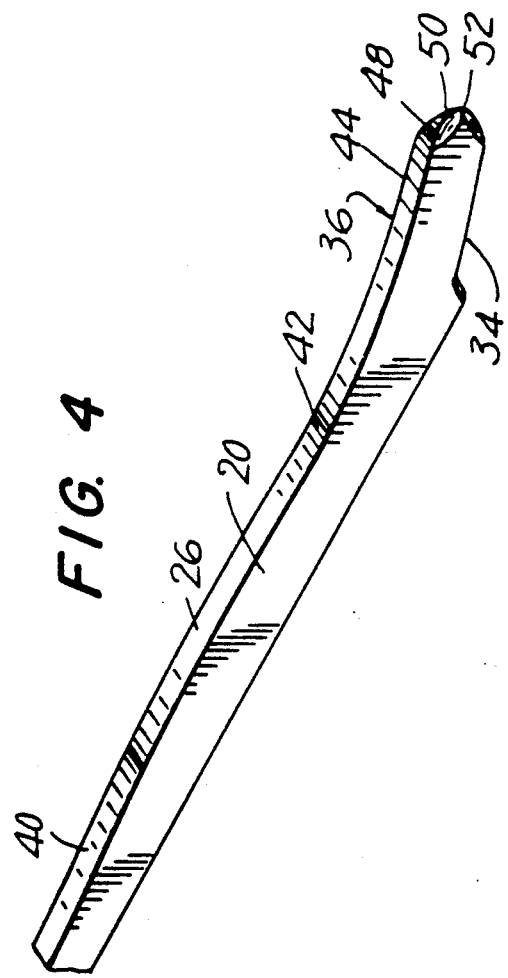
FIG. 4 is a front cutaway perspective view of a preferred embodiment for the distal end of one of the flexible outer rods of FIGS. 1 and 3.

Referring now to FIGS. 1 through 4, an intramedullary fixation device 10 for use in internal fixation of upper and lower fractures 12 and 14, respectively, involving long bones is provided. In the preferred embodiment illustrated, a long bone such as the femur 15 is being fixated. In order to closely match the changing contours of the endosteal canal 16 of a long bone and thus provide improved internal fixation, a substantially rigid center rod 18 is coupled to a plurality of generally flexible outer rods 20 using the instrumentation illustrated in FIG. 10, which will be described in more detail below. In the preferred embodiment, three outer rods 20a, 20b and 20c are provided at approximately a 120° spacing from one another (see FIG. 5).

As shown in FIGS. 1, 2, 3 and 5, center rod 18 includes a plurality of longitudinal slots 22a, b and c extending along the length thereof. In certain applications, the center rod may also include a hollow core or be cannulated. Each of the generally flexible outer rods 20a, b and c are reliably received and retained within one of the longitudinal slots. The flexible outer rods are generally of the same length as the center rod, however, in certain applications, they may be shorter.

The outer rods in this preferred embodiment are flexible rods of a constant thickness of approximately 0.125 in. It is this thickness which engages a corresponding slot 22 in the center rod thus coupling the two together. The outer rods extend above the slots of the center rod throughout its length.

Figure 3:
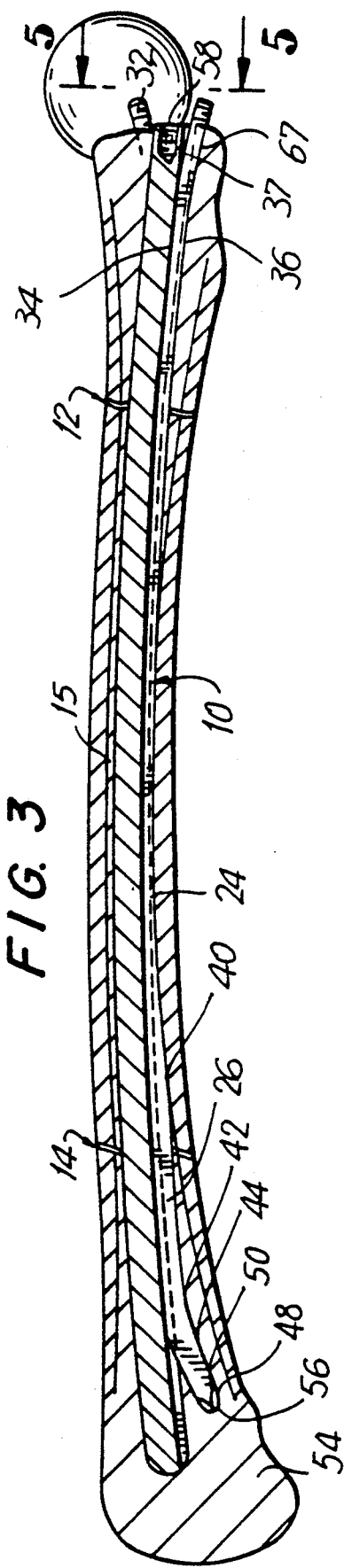
FIG. 3 is a front cross-sectional lateral view taken along line 3—3 of FIG. 1 wherein a flexible outer rod extends outwardly from a central inner rod.

The degree to which this extension occurs varies throughout the length of the implanted device because of the unique profile of the flexible outer rods. This unique profile is best described in relationship to the constant sections 24 and 26 of the rod, as shown in FIG. 3. The cross section of theses rods is essentially rectangular however the cross-section varies along the proximal 28 and distal 30 regions of the rod while remaining generally constant throughout the middle section 24 and a portion of the distal section 26.

The proximal end of the rod ends in a threaded stud 32, which is preferably approximately 0.200 in. long. For a distance of approximately 1.0 in. distal to this threaded stud the inner and outer edges 34 and 36, respectively, of the flexible outer rods converge together towards the first constant section 24 and provide for an angulated retention section 37. Typically, the inner edge of this angulated retention section 37 has a taper of generally about 4 degrees while the outer edge has a taper of generally about 10 degrees. Then over much of its length (at least about 60%) the flexible rod has a constant rectangular cross section 24 typically measuring 0.125×0.188 in. At approximately 65% of its working length the outer edge 36 of the flexible rod diverges from the longitudinal axis of the constant middle section at approximately a 3 degree angle to form divergent section 40 (see FIG. 3). The divergent section 40 continues for approximately 1.5 in. or approximately 8.5% of the overall length of the fixation device. Then for an additional 1.5 in. the cross section 26 is generally rectangular and constant measuring approximately 0.125×0.312 inches. Once again the outer edge 42 of the rod diverges from the longitudinal axis of this second constant section 26 only now at approximately a 15 degree angle to form another angulated retention section 44. Approximately 0.5 in. distal to the position 42 at which the outer edge of the rod diverges for a second time the inner edge 34 angulates away from the longitudinal axis at generally about a 20 degree angle. The inner and outer edges 34 and 36 are therefore converging and do so over the final distal 2.0 in. of the rod ending in a "rounded arrowpoint" tip 48. This rounded arrowpoint tip 48 has a cutting edge 50 at its free end 52 enabling the free end to penetrate the cancellous bone 54 within the distal end 56 of the long bone. This first or distal angulated retention section not only penetrates through the cancellous bone and the endosteal canal but is retained therein thereby stabilizing the fracture at the distal and proximal ends of the long bone. The second proximal angulated retention section 37 similarly penetrates through the proximal cancellous bone and cooperates with the distal angulated retention section to stabilize the fracture at the proximal end of the long bone.

Figure 1:
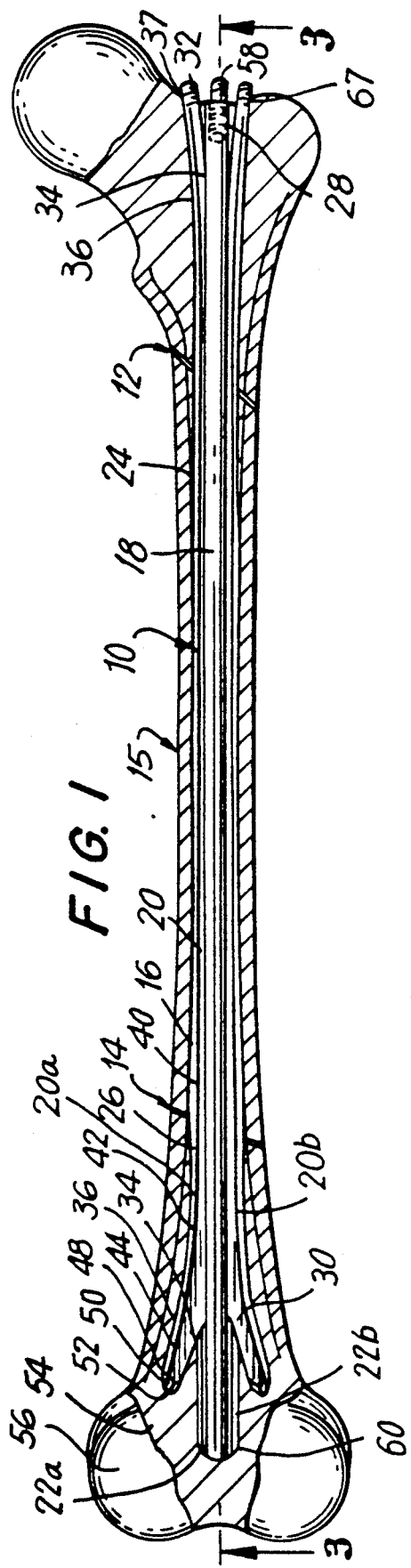
FIG. 1 is a front cross-sectional view of a preferred embodiment of the intramedullary device of the present invention installed within a long bone.
Figure 2:
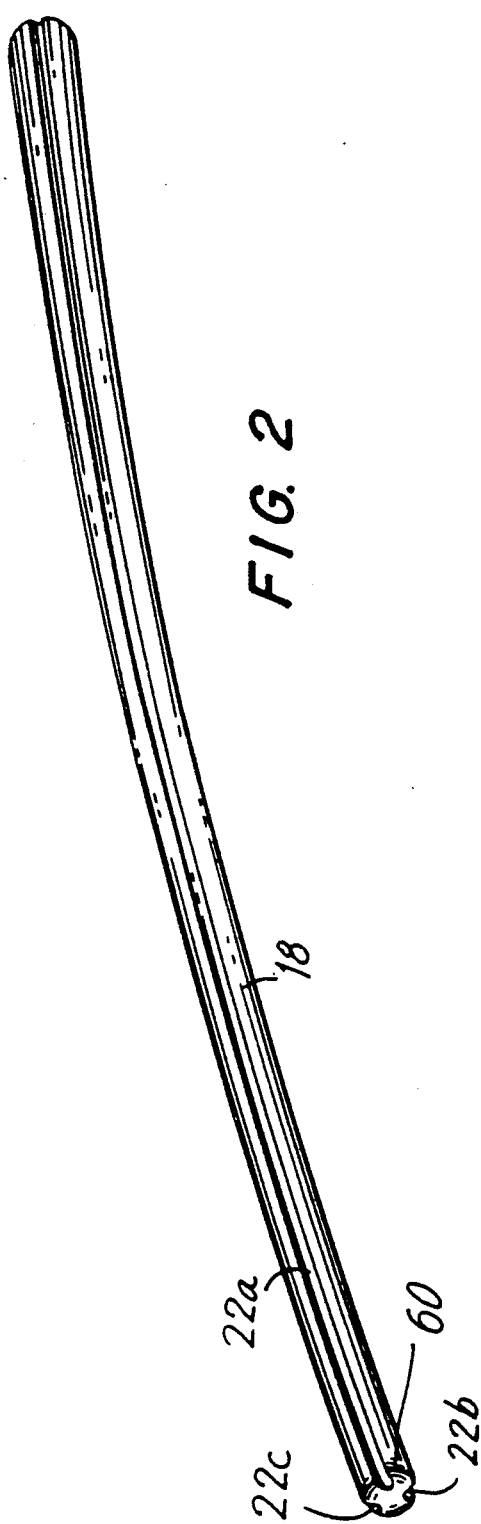
FIG. 2 is a front perspective view of the substantially rigid center rod 18 of FIG. 1.

The center rod is essentially circular in cross section (see FIG. 2). It has a slight anterior curvature to conform to the "anterior bow" of the femur. Similarly, the flexible outer rods have a slight curvature as well to conform to the curvature of the center rod. The longitudinal slots 22a, b and c are preferably approximately 0.125 in. deep ×0.130 wide along their entire length. At its proximal end these slots converge toward the longitudinal axis of the center rod at an angle of approximately 4 degrees for a distance of 1.0 in. which corresponds to the same region over which the flexible rods converge at their proximal ends. A hole 58 is drilled and tapped in the proximal end of the rod for a depth of typically 0.5 in. in order to connect it to the instrumentation used for installation and removal (FIG. 10). At its distal end 60, the rod is rounded for ease of installation. In this preferred embodiment both the outer and center rods are made of stainless steel however other materials such as titanium alloys (T-6AL-4V), cobalt-chromium alloys or composite materials can be utilized. In order to stabilize femurs of varying length and diameters, the center rod can be variably sized in length as well as in diameter. Similarly, the flexible outer rods will be of variable lengths each corresponding to the length of the center rod required to stabilize the fracture.

A second preferred embodiment of the IM device of this invention is illustrated in FIGS. 6-9. This IM device is particularly well-suited in those instances where because of the fracture, virtually no wall of the endosteal canal remains. The design of this IM device is substantially the same as the IM device of FIGS. 1-5 except for the following differences. In order to provide for significant retention at the proximal end 62 of the long bone, a plurality of screw pins 64a, b and c are laterally screwed into one of a plurality of laterally orifices 66a, b and c within the substantially rigid center rod. In order to provide better retention capabilities of the flexible outer rods 20a', b' and c' within the longitudinal slots 22a', b' and c', the flexible outer rods are in cross section a generally inverted T-shape which conforms with the same cross-section of the longitudinal slots. As such, this design provides for the loss in this instance of the stabilizing effect on the outer rods provided in the usual fracture by the endosteal wall.

The unique instrumentation required for the installation and removal of this new intramedullary device is best described and understood in the step wise fashion that it is used during such a procedure. This installation instrumentation is illustrated in FIGS. 10 and 11. In the case of the femur the proximal femur is approached in a standard fashion. A hole 67 is made in the region of the piroformis fossa in the usual manner and a guide wire passed across the fracture site. It may be desirable to ream the intramedullary canal since it has been shown beneficial to use implants of larger diameters in the case of the femur. Reaming is not however a prerequisite for the installation of this device. In fact because the device "expands" in the proximal and distal regions of a long bone impinging on the endosteal surface it can be installed in a non-reamed fashion. This has obvious advantages particularly if a similar device were to be used in the case of the tibia with its already precarious blood supply and the increasing demands placed upon the orthopedist to stabilize these fractures.

Whether one reams or not, the installation proceeds in the following manner. First, one of a plurality of extension rods 70a, b and c is threaded onto each of the outer flexible rods 20a, b and c, respectively. The outer rods are then introduced via the hole in the piroformis fossa and passed across the fracture site(s) one at a time. If reaming was performed the guide wire should be removed after the first outer rod is introduced and across the fracture site. As each outer rod is introduced care should be taken in positioning the inner edge towards the center of the canal. Furthermore, the rods are placed at approximately 120 degree intervals around the endosteal canal. These last two steps facilitate coupling to the center rod and instrumentation. It should be noted that at this point the outer rods are past the fracture site(s) and in the region of the metaphysis but not at their final depth-the region of the femoral condyles with its dense cancellous bone. Next an adaptor 72 is fastened to the end of each extension rod with three thumb screws 74. The center rod can now be loaded onto the outer rods by inserting it through the central opening 76 in the adaptor (see FIG. 11). At this point the center rod can be tapped approximately ⅓ of the way down the intramedullary canal with a plastic mechanic's mallet. Care should be taken to insure that as the center rod is advanced it is properly engaging the outer rods.

The remainder of the instrumentation which includes a threaded rod 78, a cylindrical sleeve 80 and housing 82 for two thrust bearings 84, an internally threaded sleeve 86 onto which the thrust bearings mount and a slide hammer 88 are installed as a unit as shown in FIG. 10. The slide hammer 88 is now used to advance the entire assembly down the medullary canal until the flexible outer rods are at their final depth retained within the cancellous bone. The threaded rod of the instrumentation has a necked down tip 90 which is threaded (RH)

into the tapped hole 58 in the proximal end of the center rod. The threaded end of the outer sleeve 92 screws into the base 94 of the adaptor. A long deep socket 96 is connected to the internally threaded sleeve 86 on one end and a power drill (not shown) on the other. In the case of a LH assembly (a left handed (LH) threaded rod coupled to a left handed (LH) internally threaded sleeve 86), the internally threaded sleeve 86 rotated clockwise will thread or advance the threaded rod 78 since the internally threaded sleeve is held at a fixed length by means of the cylindrical sleeve 80. As the threaded rod advances, the center rod is pushed down the medullary canal.

Due to the anterior bow of the femur, as the center rod is advanced, the threaded rod tends to migrate in a radial fashion potentially abutting the inner diameter of the cylindrical sleeve 80. The thrust bearings 84 and their housing 82 alleviate not only this radial migration but also aid in eliminating friction present between the internally threaded sleeve 86 and the cylindrical sleeve 80. The length of the cylindrical sleeve is predetermined so that the slide hammer 88 has a reasonable working length. Left handed and right handed threaded rods are employed in order that installation and removal, respectively, of the device is accomplished with a standard (forward or clockwise) power drill, thus insuring a positive lock between the necked down tip 90 of the threaded rod and the center rod 18. As the center rod advances the flexible outer rods are forced up against the endosteal wall. In the sense the implant in now "expanding"0 in diameter in the proximal and to a much greater degree in the distal regions of the femur. From the installation of the first outer rod until the center rod is completely down the canal takes approximately 5 minutes.

There are several advantages to this unique instrumentation. First the installation of the center rod is accomplished in a very smooth fashion. Currently all IM devices are hammered down the intramedullary canal often times causing iatrogenic fractures or propagating existing ones. Furthermore, it has recently been shown that removal of IM devices particularly the more rigid ones can be hazardous and lead to iatrogenic new fractures after the primary fracture has healed. Removal of this device is as smooth as installation the only difference being that a RH threaded rod is used for removal. Lastly since the orthopedist is installing a device which "expands" in its diameter care must be taken that the device is not too large for the bone being stabilized. Since this instrumentation essentially uses a jack-screw mechanism for the installation of the center rod the operator can monitor the torque required for advancement of the center rod. If this seems excessive to the operator he/she can stop; assess the situation and make the necessary adjustments.

In its implanted position, the IM device of this invention also provides for other additional significant advantages. First, while providing excellent stabilization throughout the length of the medullary canal the endosteal surface is not suffocated with hardware. The device only impinges on the endosteal canal at the 3 outer edges of the flexible outer rods. This feature has been shown to be important in the revascularization of the medullary canal following IM nailing whether it is done in a reamed on non-reamed fashion. Secondly, while the present invention particularly addresses distal and proximal fracture patterns it does not ignore fracture patterns of the mid-shaft. Since the outer flexible rods "ride" above the slots in the center rod in this region they impinge on the endosteal surface and thus provide excellent stabilization in this region as well. Thirdly, it should be noted that distally the implanted device effectively has "expanded" $2\frac{1}{2}$ times the diameter of the intramedullary canal at the isthmus—i.e. its narrowest diameter. Finally in its implanted position the device has a very low profile externally. Many of the currently used IM devices must protrude a significant distance out of the proximal femur in order to be removed later which often times causes premature hardware problems.

While the preferred embodiment of the present invention has been described, it should be understood that various changes, adaptations and modifications may be made therein without departing from the spirit of the invention and the scope of the appended claims. It is intended that the appended claims be interpreted as including the foregoing as well as various other such changes and modifications.

What is claimed is:

1. An intramedullary fixation device for use in internal fixation of various fracture patterns involving the longitudinal axis of a long bone and including distal and proximal ends thereof comprising:
   a substantially rigid center rod having a plurality of longitudinal slots extending along the length thereof;
   a plurality of generally flexible outer rods extending outwardly from said center rod, each said outer rod being received and retained within one of said longitudinal slots and having a distal retention section angulated from the longitudinal axis which penetrates through and is retained by the cancellous bone and the endosteal canal thereby stabilizing the fracture at the distal and proximal ends of the long bone.

2. The intramedullary fixation device as set forth in claim 1 wherein each said outer rod has a thickness of approximately 0.125 in.

3. The intramedullary fixation device as set forth in claim 1 wherein said rigid center rod has an anterior curvature generally corresponding to an anterior bow of the long bone.

4. The intramedullary fixation device as set forth in claim 3 wherein each said outer rod has a curvature which substantially corresponds to the curvature of said rigid center rod.

5. The intramedullary fixation device as set forth in claim 1 wherein each said outer rod has a first generally constant cross-section portion along the majority of its length generally parallel to said longitudinal axis.

6. The intramedullary fixation device as set forth in claim 5 wherein said first generally constant cross-section portion has a dimension of approximately $0.125 \times 0.188$ in.

7. The intramedullary fixation device as set forth in claim 5 wherein each said outer rod has a second portion extending upwardly from said first generally constant cross-section portion at an angle of approximately 3 degrees from said longitudinal axis.

8. The intramedullary fixation device as set forth in claim 7 wherein said second portion begins at approximately 65% of the working length of said outer rod and extends approximately 1.5 inches.

9. The intramedullary fixation device as set forth in claim 7 wherein each said outer rod has a third generally constant cross-section portion generally parallel to the longitudinal axis which extends from said second portion for approximately 1.5 inches.

10. The intramedullary fixation device as set forth in claim 9 wherein each said outer rod has a fourth portion extending upwardly from said third generally constant cross-section portion at an angle of approximately 15 degrees from said longitudinal axis.

11. The intramedullary fixation device as set forth in claim 10 wherein each said outer rod has a fifth portion defining said retention section and extending upwardly from said fourth portion at an angle of approximately 20 degrees from said longitudinal axis.

12. The intramedullary fixation device as set forth in claim 1 wherein said retention section has a cutting mean at its free end enabling said free end to penetrate the cancellous bone.

13. The intramedullary fixation device as set forth in claim 12 wherein said cutting means is in the form of a generally rounded arrowpoint.

14. The intramedullary fixation device as set forth in claim 1 wherein said flexible outer rods can be shorter in length than said center rod.

15. The intramedullary fixation device as set forth in claim 1 wherein said center rod includes a hollow core.

16. The intramedullary fixation device as set forth in claim 1 wherein said center rod is cannulated.

17. An intramedullary fixation device for use in internal fixation of various fracture patterns involving the longitudinal axis of a long bone having distal and proximal ends thereof comprising:
a substantially rigid center rod having a plurality of generally inverted T-shaped slots extending substantially along the length thereof;
a plurality of generally flexible outer rods extending outwardly from said center rod, each said outer rod having a generally T-shaped cross section and thereby being received and retained within one of said center rod slots, each said outer rod also having a retention section angulated from the longitudinal axis which penetrates through and is retained by the cancellous bone thereby stabilizing the fracture at the distal and proximal ends of the long bone.

18. The intramedullary fixation device as set forth in claim 17 wherein said retention section has a cutting means at its free end in the form of a generally rounded arrowpoint tip enabling said free end to penetrate the cancellous bone.

19. The intramedullary fixation device as set forth in claim 17 wherein said center rod includes a plurality of lateral orifices tapped therethrough which provide for increased proximal fixation.

20. An intramedullary fixation and installation device for use in internal fixation of various fracture patterns involving the longitudinal axis of a long bone having a endosteal canal comprising:
an installation device having a plurality of extension rods and a center rod loading means;
a plurality of generally flexible outer rods coupled to said installation device and extending into said endosteal canal with an end of each outer rod being cooperatively engaged by one of said extension rods and the other end having a cutting means;
a generally rigid center rod introduced through said loading means into said endosteal canal, said center rod having a plurality of longitudinal slots into which one of said outer rods is slidably engaged whereby as said center rod is moved into the endosteal canal, said cutting means penetrates through the cancellous bone and permits said retention section to be retained within the cancellous bone thereby stabilizing the fracture of the long bone.

21. This intramedullary fixation and installation device of claim 20 wherein said installation device includes a slide hammer means which is movable between a rest position and a forward position wherein said inner rod and plurality of outer rods are advanced forwardly until said flexible outer rods are retained within the cancellous bone.

22. The intramedullary fixation and installation device of claim 20 wherein said installation device includes power means operatively connected to said center rod to drive said center rod into the endosteal canal and thus force said outer rods against the endosteal wall.

23. The intramedullary fixation and installation device of claim 20 wherein said installation device includes a threaded rod, a cylindrical sleeve coupled to said threaded rod and an internally threaded sleeve held at a fixed length by said cylindrical sleeve and coupled to said threaded rod such that as said internally threaded sleeve is rotated clockwise, the threaded rod advances.

24. The intramedullary fixation and installation device of claim 23 wherein said threaded rod has a necked down tip which is threaded into a tapped hole in the proximal end of said center rod.

25. The intramedullary fixation and installation device of claim 23 wherein a pair of thrust bearings are mounted to said internally threaded sleeve thereby eliminating friction between said cylindrical sleeve and said internally threaded sleeve.

* * * * *